United States Patent [19]

Thierman

[11] Patent Number: 4,483,676
[45] Date of Patent: Nov. 20, 1984

[54] INTERPROXIMAL DENTAL INSTRUMENT

[76] Inventor: Robert B. Thierman, P.O. Box 03371, Portland, Oreg. 97203

[21] Appl. No.: 471,764

[22] Filed: Mar. 3, 1983

[51] Int. Cl.³ .............................................. A61C 3/06
[52] U.S. Cl. .................................................. 433/142
[58] Field of Search .................. 433/142, 144; 132/92, 132/93

[56] References Cited

U.S. PATENT DOCUMENTS

| 1,050,469 | 1/1913 | Keifer | 433/142 |
| 1,201,875 | 10/1916 | Russ | 433/142 |
| 1,350,002 | 8/1920 | Burlew | 433/142 |
| 2,730,804 | 1/1956 | Saupe | 433/142 |
| 3,771,537 | 11/1973 | Schole | 132/93 |
| 4,030,198 | 6/1977 | Gerber | 433/142 |

FOREIGN PATENT DOCUMENTS

| 377764 | 6/1923 | Fed. Rep. of Germany | 433/142 |
| 2018603 | 10/1979 | United Kingdom | 433/142 |

Primary Examiner—Robert Peshock
Attorney, Agent, or Firm—Eugene M. Eckelman

[57] ABSTRACT

A disc of semi-rigid material has side surfaces and a rounded working edge. The disc has minimum thickness allowing it to be forced into the contact areas between teeth for smoothening such areas and also allowing the working edge to remove excess bonding material in proximal areas. The disc is provided with a grip on the end opposite from the working edge. One or both of the side surfaces of the disc has abrasive means to assist in smoothening the contact areas. The instrument has an aperture therethrough for tying a retrieving line thereto. The grip is installed on the disc by injection molding, the disc having a pair of apertures therein through which molded plugs of the grip connect the side portions of the grip together and also securely attach the grip to the disc.

The disc has also been used as a matrix in special cases so as to keep contact area free of excess restorative material.

3 Claims, 4 Drawing Figures

U.S. Patent Nov. 20, 1984 4,483,676
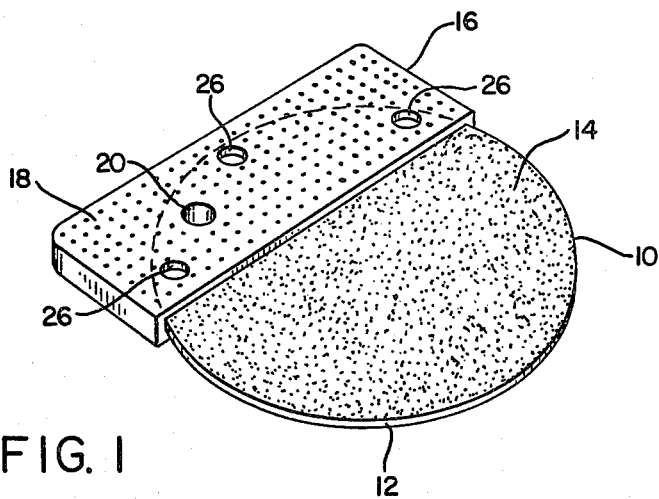
FIG. 1
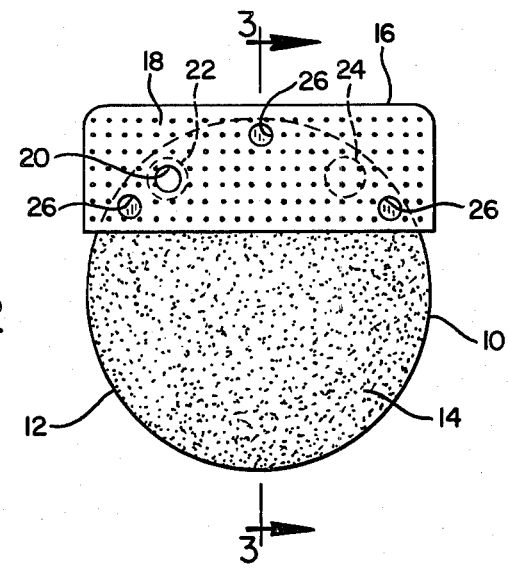
FIG. 2
FIG. 3
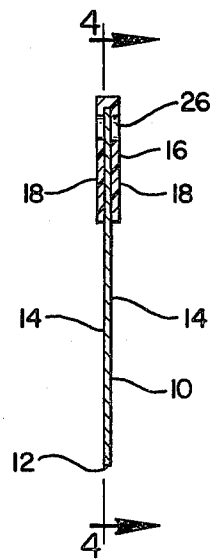
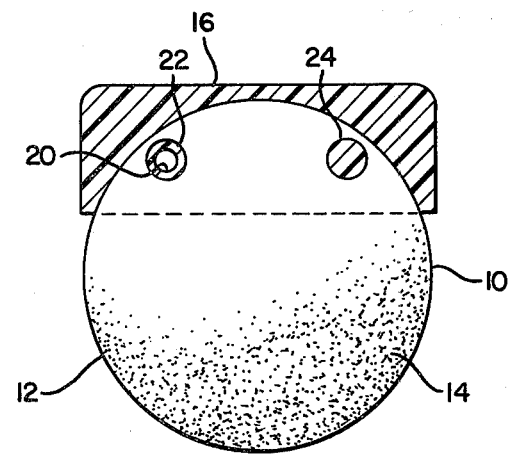
FIG. 4

INTERPROXIMAL DENTAL INSTRUMENT

BACKGROUND OF THE INVENTION

This invention relates to a new and novel interproximal dental instrument.

As is apparent, the areas between the teeth are often rough and have overhangs which make it difficult to operate dental floss between the teeth. Dentists who use rubber dams are also aware of such rough areas since it is difficult to insert the dams. These rough areas may be the result of natural improperly formed surfaces or by restorations with overhangs such as fillings. Dentists, of course, attempt to make or keep these surfaces smooth so that it is possible to floss with ease as well as to allow insertion of rubber dams for tooth repair, but frequently due to natural or corrective dentistry, the contact areas become rough and excess bonding from fillings exist. Dentists have heretofore used various types of tools and implements in an attempt to smoothen the contact areas between the teeth as well as to remove or smoothen excess bonding material from fillings. Such tools, however, are not capable of efficiently providing the smooth contact desired as well as to efficiently remove excess bonding material.

SUMMARY OF THE INVENTION

According to the present invention and forming a primary objective thereof, an interproximal dental instrument is provided that is capable efficiently of smoothening the contact areas of the teeth and also capable of removing excess bonding material from fillings or other restorations.

Another object is to provide an instrument of the type described that is simplified in structure and also simplified in its use.

Another object is to provide an instrument of the type described that by its structure is capable of manufacture in a novel manner.

In carrying out the objectives of the invention, the interproximal dental instrument comprises a disc constructed of semi-rigid metal having abrasive side surfaces and a rounded working edge. The disc has a minimum thickness such that it can be forced into the contact areas between teeth for smoothening such areas. The working edge can also be used to remove excess bonding material in proximal areas of the teeth. The disc is provided with a grip portion with roughened side surfaces which provide a good friction grip for the dentist's fingers. The grip is attached to the disc by an injection molding process, and for this purpose, the disc has aperture means for receiving plugs molded therein for connecting side portions of the grip together and also for securely attaching the grip to the disc. The instrument has an aperture therethrough for attachment of a retrieving line.

The invention will be better understood and additional objects and advantages will become apparent from the following description taken in connection with the accompanying drawings.

BRIEF DESCRIPTION OF THE DRAWINGS

FIG. 1 is a perspective view of the interproximal dental instrument embodying features of the invention;

FIG. 2 is a side elevational view of the instrument;

FIG. 3 is a sectional view taken on the line 3—3 of FIG. 2; and

FIG. 4 is a sectional view taken on the line 4—4 of FIG. 3.

DETAILED DESCRIPTION OF A PREFERRED EMBODIMENT

The working portion of the present dental instrument comprises a metal disc 10 having a rounded working edge 12. The disc 10 is constructed of rigid or semi-rigid metal and has a uniform thickness. A thickness of 0.005 inch has been found to be satisfactory, although slight variance thereof may be used. Such thickness is found to be capable of insertion through the contact areas of the teeth and also of working in the space or proximal areas between the teeth for clearing out excess bonding material that may be present, as will be set forth in greater detail hereinafter. Although the size of the disc as to the diameter thereof may vary, a diameter of approximately three-quarters inch provides efficient functioning of the instrument, as will also be more apparent hereinafter.

The side surfaces 14 of the disc are roughened so as to provide an abrasive area for the purpose of smoothening the contact areas between the teeth. In those contact areas that are very tight, a slight expansion of the areas may be desirable. The disc may be provided with the abrasive surface on one or both sides. Such abrasive surface or surfaces comprise a very fine sandpaper-like surface and usually merely are required to polish the contact areas so as to allow insertion of dental floss or rubber dams, although as stated some expansion of the contact areas may be accomplished. The roughened surfaces 14 may be formed by sand blasting.

Disc 10 is provided with a grip 16 comprising a cap-like member which covers the non-working edge of the disc. This grip has roughened side surfaces 18 providing a friction grip for the dentist's fingers. The assembly of disc 10 and grip 16 includes an aperture 20 therethrough serving as a tie hole allowing the dentist to tie a piece of floss or the like to the instrument for the purpose of retrieving the instrument in the event that it should be accidentally dropped in the patient's mouth.

A novel form of assembly is provided to form the disc 10 and its grip 16. As best seen in FIG. 4, the disc 10 is manufactured in circular form, as by stamping, and as manufactured, it is made with two holes 22 and 24 in the grip area. The grip 16 is molded directly on the disc 10 with the material of the grip being molded around the upper portion of the disc and also through the two holes 22 and 24, the tie hole 20 being maintained by a suitable mold insert. Guide fingers in the mold leave impressions 26 in the side surfaces 18 of the grip and these impressions add to the friction hold on the grip 16.

With the mold material for the grip 16, such as a suitable plastic, embedded around the upper portion of the disc as well as through the holes 22 and 24, a positive connection is provided between the disc and the grip to insure that there will be no accidental separation of these members.

In the use of the present disc, the dentist, with a firm grip on the portion 16, forces the working edge of the disc 10 through the contact area of the teeth and with one or more parallel movements in such area, any roughness is smoothened down so that flossing can be efficiently carried out without fraying or breaking and also rubber dams can be readily inserted. By further penetration of the disc through the contact area, the disc can be used to clear out any excess bonding material in the proximal areas. Although the working edge of the instrument is not sharpened, it has sufficient sharpness due to the thinness of the disc to work through or push out any excess bonding material. The disc when made of sheet metal in a thickness of approximately 0.005 inch provides this efficient functioning and while having sufficient rigidity to be pushed edgewise through the contact area without creasing can at the same time flex slightly to move past obstructions on the teeth.

The diameter of the disc, namely, approximately three quarters inch, provides an instrument such that when gripped between the fingers maintains a projecting working distance that will efficiently smoothen contact areas or clean the area between teeth but also will not project through the area to damage gingival areas or the torque since the fingers will abut against the tooth to form a safety stop.

The disc can also be used as a matrix in special cases so as to keep contact areas free of excess restorative material.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. An interproximal dental instrument comprising
   a disc of semi-rigid metal having side surfaces and a rounded working edge at one end,
   one of said side surfaces of said disc being roughened to provide an abrasive area,
   said disc having a thickness of approximately five thousandths inch allowing it to be forced into the contact areas between teeth for smoothening such areas and also allowing the working edge to remove excess bonding material in proximal areas of the teeth,
   and a grip member secured on said disc on the end opposite from said working edge,
   said grip having roughened side surfaces to provide a friction grip thereon between the fingers,
   the rigidity of said disc being such that it can be forced edgewise through the contact areas of the teeth but at the same time said disc can bend slightly to move past obstructions on the teeth.

2. The interproximal dental instrument of claim 1 wherein said disc and grip have an aperture therethrough for tying a retrieving line to the instrument.

3. The interproximal dental instrument of claim 1 wherein said grip comprises a plastic portion molded on both sides of said disc, said disc having a pair of apertures for receiving molded plugs therethrough for connecting the side portions of the grip and securely attaching said grip to said disc, one of said plugs being apertured for tying a retrieving line to the instrument.

* * * * *